United States Patent
Wild et al.

(10) Patent No.: US 7,846,674 B2
(45) Date of Patent: *Dec. 7, 2010

(54) ASSESSING RHEUMATOID ARTHRITIS BY MEASURING ANTI-CCP AND INTERLEUKIN 6

(75) Inventors: Norbert Wild, Geretsried/Gelting (DE); Viet Peter Grunert, Munich (DE); Johann Karl, Peissenberg (DE); Werner Zolg, Weilheim-Unterhausen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 594 days.

This patent is subject to a terminal disclaimer.

(21) Appl. No.: 11/472,069

(22) Filed: Jun. 21, 2006

(65) Prior Publication Data

US 2007/0264673 A1    Nov. 15, 2007

Related U.S. Application Data

(63) Continuation of application No. PCT/EP2004/014527, filed on Dec. 21, 2004.

(30) Foreign Application Priority Data

Dec. 23, 2003    (EP)    ............... 03029658

(51) Int. Cl.
*G01N 33/53*    (2006.01)
(52) U.S. Cl. ............ 435/7.1; 435/7.2; 436/518
(58) Field of Classification Search .......... 435/7.1, 435/7.2, 7.91, 7.92
See application file for complete search history.

(56) References Cited

U.S. PATENT DOCUMENTS

| | | | |
|---|---|---|---|
| 4,208,479 A * | 6/1980 | Zuk et al. | ............. 435/7.9 |
| 4,755,380 A * | 7/1988 | Grubb et al. | ............. 530/328 |
| 6,017,693 A | 1/2000 | Yates, III et al. | |
| 6,309,888 B1 | 10/2001 | Holvoet et al. | |
| 6,410,724 B1 | 6/2002 | Dejean et al. | |

(Continued)

FOREIGN PATENT DOCUMENTS

EP    1107006 A1    6/2001

(Continued)

OTHER PUBLICATIONS

Leeuwen et al. (Annals Rheumatic Disease 1996 vol. 54, p. 674-677.*

(Continued)

*Primary Examiner*—Jacob Cheu

(57) ABSTRACT

The present invention relates to a method aiding in the assessment of rheumatoid arthritis. The method especially is used in assessing the absence or presence of rheumatoid arthritis in vitro. The method is for example practiced by analyzing biochemical markers, comprising measuring in a sample the concentration of anti-CCP and interleukin 6 and correlating the concentrations determined to the absence or presence of rheumatoid arthritis. To further improve the assessment of RA in a method of this invention the level of one or more additional marker may be determined together with anti-CCP and interleukin 6 and be correlated to the absence or presence of RA. The invention also relates to the use of a marker panel comprising anti-CCP and interleukin 6 in the diagnosis of rheumatoid arthritis and it teaches a kit for performing the method of the invention.

4 Claims, 5 Drawing Sheets

U.S. PATENT DOCUMENTS

| | | | |
|---|---|---|---|
| 2002/0072492 | A1 | 6/2002 | Myers et al. |
| 2003/0224386 | A1* | 12/2003 | Guild et al. ............... 435/6 |

FOREIGN PATENT DOCUMENTS

| | | | |
|---|---|---|---|
| EP | 0654092 | B1 | 9/2003 |
| WO | WO 98/08946 | | 3/1998 |
| WO | WO 98/22503 | | 5/1998 |
| WO | WO 99/28344 | | 6/1999 |
| WO | WO 99/35167 | | 7/1999 |
| WO | WO 01/46222 | A2 | 6/2001 |
| WO | WO 01/94616 | A1 | 12/2001 |
| WO | WO 02/06840 | A2 | 1/2002 |
| WO | WO 02/23200 | A2 | 3/2002 |
| WO | WO 02/48310 | A2 | 6/2002 |
| WO | WO 03/050542 | A2 | 6/2003 |
| WO | WO 03/060465 | A2 | 6/2003 |
| WO | WO 03/069341 | A2 | 8/2003 |
| WO | WO 2005029091 | * | 3/2005 |

OTHER PUBLICATIONS

Schellekens et al. (Arthritis & Rheumatism 2000 vol. 43, p. 155-163).*

J. Clinical Laboratory Analysis 2000 vol. 14, p. 305-313.*

Liao et al. Hepatobiliary Pancreat Dis Int. 2007 vol. 6, p. 641-645.*

Landers et al. Int. J. Cancer 2005 vol. 114, p. 950-956.*

Swaak et al. (J. Scan. Rheumatol. 1988 vol. 469-474.*

An Introduction to Classification Regression Tree Analysis ( by Lewis, PhD. presentation date 2000 at the annul meeting for the society of emergency medicine; p. 1-14.*

Madhok et al. Annals Rheumatic Diseases 1993 vol. 52, p. 232-234.*

Migita et al. Lab. Investigation 1998 vol. 78, p. 535-539.*

McLachlan, G., "Discriminant Analysis and Statistical Pattern Recognition", bibliographic data, John Wiley & Sons, Inc., 1992.

Al-Dehaimi, A. et al., "Serum Galactosyl Hydroxylysine as a Biochemical Marker of Bone Resorption," Clinical Chemistry 45:5, 676-681 (1999).

Arnett, F. et al., "The American Rheumatism Association 1987 Revised Criteria for the Classification of Rheumatoid Arthritis," Arthritis and Rheumatism, vol. 31, No. 3 (Mar. 1988) 315-324.

Ballara, S. et al., "Raised Serum Vascular Endothelial Growth Factor Levels are Associated with Destructive Change in Inflammatory Arthritis," Arthritis & Rheumatism, vol. 44, No. 9, Sep. 2001, 2055-2064.

Bartfield, H. et al., "Distribution of Rheumatoid Factor Activity in Nonrheumatoid States," Ann. NY Acad. Sci. 168(1969) 30-40.

Bas, S. et al., "Comparative study of different enzyme immunoassays for measurement of IgM and IgA rheumatoid factors," Ann Rehum Dis 2002; 61, 505-510.

Bas, S. et al., "Diagnostic tests for rheumatoid arthritis: comparison of anti-cyclic citrullinated peptide antibodies, anti-keratin antibodies and IgM rheumatoid factors," Rheumatology 2002; 41: 809-814.

Billinghurst, R. et al., "Enhanced Cleavage of Type II Collagen by Collagenases in Osteoarthritic Articular Cartilage," J. Clin. Invest. 99 (1997)1534-1545.

Bizzaro, N. et al., "Diagnostic Accuracy of the Anti-Citrulline Antibody Assay for Rheumatoid Arthritis," Clinical Chemistry, 47:6, 1089-1093 (2001).

Bonde, M. et al., "Immunoassay for Quantifying Type I Collagen Degradation Products in Urine Evaluated," Clin.Chem. 40/11, 2022-2025 (1994).

Breiman, L.,"Random Forests," Machine Learning, 45, 5-32, 2001.

Brenchley, P. et al., "Angiogenesis in inflammatory joint disease: a target for therapeutic intervention," Clin Exp Immunol 2000, 121:426-429.

Burmeister, G. et al., "A Selective Method for Determining MRP8 and MRP14 Homocomplexes and Heterocomplexes by Sandwich Elisa for the Discrimination of Active and Non-Active Osteoarthritis from Rheumatoid Arthritis in Sera and Synovial Fluids," Inflammapharmacology, 1995; 3: 221-230.

Chabas, D. et al., "The Influence of the Proinflammatory Cytokine, Ostopontin, on Autoimmune Demyelinating Disease," Science, vol. 294, Nov. 23, 2001, 1731-1735.

Foell, D. et al., "Expression of the pro-inflammatory protein S100A12 (EN-RAGE) in rheumatoid and psoriatic arthritis," Rheumatology, 2003; 42:1383-1389.

Friedman, J., "Regularized Discriminant Analysis," Journal of the American Statistical Association, Mar. 1989, 165-175.

Gineyts, E., "Urinary excretion of glucosyl-galactosyl pyridinoline: a specific biochemical marker of synovium degradation," Rheumatology 2001; 40:315-323.

Gundberg, C., "Biology, Physiology, and Clinical Chemistry of Osteocalcin," Journal of Clinical Ligand Assay, vol. 21, No. 2, Summer 1998.

Hochberg, M. et al., "The American College of Rheumatology 1991 Revised Criteria for the Classification of Global Functional Status in Rheumatoid Arthritis," Arthritis and Rheumatism, vol. 35, No. 5 (May 1992) 498-502.

Ishiguro, N. et al., "Relationships of Matrix Metalloproteinases and Their Inhibitors to Cartilage Proteoglycan and Collagen Turnover and Inflammation as Revealed by Analyses of Synovial Fluids from Patients with Rheumatoid Arthritis," Arthritis & Rheumatism, vol. 44, No. 11, Nov. 2001, pp. 2503-2511.

Johansen, J. et al., "Serum YKL-40 concentrations in patients with early rheumatoid arthritis: relation to joint destruction," Scand J Rheumatol 2001; 30: 297-304.

Jorgensen, C. et al., "IgA isotype rheumatoid factor in rheumatoid arthritis: clinical implications," Clinical and Experimental Rheumatology 14: 301-304, 1996.

Kaufmann, J. et al., "Hydroxypyridinium collagen crosslinks in serum, urine, synovial fluid and synovial tissue in patients with rheumatoid arthritis compared with osteoarthritis," Rheumatology 2004; 42: 314-320.

Kellgren, J. et al., "Radiological Assessment of Osteo-Arthritis," Ann. Rheum. Dis (1957) 16,494-502.

Knott, L. et al., "Collagen Cross-Links in Mineralizing Tissues: A Review of Their Chemistry, Function and Clinical Relevance," Bone vol. 22, No. 3, Mar. 1998: 181-187.

Lee, S. et al., "Vascular endothelial growth factor levels in the serum and synovial fluid of patients with rheumatoid arthritis," Clinical and Experimental Rheumatology: 2001; 19: 321-324.

Lorenzo, P. et al., "A Novel Cartilage Protein (CILP) Present in the Mid-Zone of Human Articular Cartilage with Age," The Journal of Biological Chemistry, vol. 273, No. 36, Sep. 4, 1998, 23463-23468.

Moore, T. et al., "Rheumatoid Factors," Clin. Biochem., vol. 26, pp. 75-84, 1993.

Muller-Ladner, U. et al., "MIA (melanoma inhibitory activity): a potential serum marker for rheumatoid arthritis," Rheumatology 1999; 38:148-158.

Petrow, P. et al., "Expression of Osteopontin Messenger RNA and Protein in Rheumatoid Arthritis," Arthritis & Rheumatism, vol. 43, No. 7, Jul. 2000, p. 1597-1605.

Rantapaa-Dahlqvist, S. et al., "Antibodies Against Cyclic Citrullinated Peptide and IgA Rheumatoid Factor Predict the Development of Rheumatoid Arthritis," Arthiritis & Rheumatism, vol. 48, No. 10, Oct. 2003, pp. 2741-2749 .

Ruczinski, I. et al., "Logic Regression," Journal of Computational Graphical Statistics, vol. 12, No. 3, pp. 475-511, 2003.

Horneff, G. et al. "Reduction of monocyte-macrophage activation markers upon anti-CD4 treatment. Decreased levels of Il-1, Il-6, neopterin and soluble CD14 in patients with rheumatoid arthritis," Clin Exp. Immunol. 1993: 91: 207-213.

Sawai, T. et al., "Dynamics of Hyaluronate in Patients with Rheumatoid Arthritis," Connective Tissue, vol. 33, 2001, 253-259.

Saxne, T. et al., "Cartilage Oligomeric Matrix Protein: A Novel Marker of Cartilage Turnover Detectable in Synovial Fluid and Blood," British Journal of Rheumatology, 1992; 31, 583-591.

Saxne, T. et al., "Increased Release of Bone Sialoprotein into Synovial Fluid Reflects Tissue Destruction in Rheumatoid Arthritis," Arthitis & Rheumatism, vol. 38, No. 1, Jan. 1995, p. 82-90.

Schellekens, G. et al., "The Diagnostic Properties of Rheumatoid Arthritis Antibodies Recognizing a Cyclic Citrullinated Peptide," Arthritis & Rheumatism, vol. 43, No. 1, Jan. 2000, pp. 155-163.

Schumacher, H., "Palindromic Onset of Rheumatoid Arthritis," Arthritis & Rheumatism, vol. 25, No. 4, Apr. 1982, p. 361-369.

Hastie, et al., "The Elements of Statistical Learning," Springer Series in Statistics, 2001.

Straub, R. et al., "Decrease of Interleukin 6 During the First 12 Months is a Prognostic Marker for Clinical Outcome During 36 Months Treatment with Disease-Modifying Anti-Rheumatic Drugs," British Journal of Rheumatology 1997: 36:1298-1303.

Suzuki, F., Roles of Cartilage Matrix Proteins, Chondromodulin-I and -II, in Endochondral Bone Formation: A Review, Connective Tissue Research, vol. 35(1-4) pp. 303-307, 1996.

Swedler, W. et al., "Routine Measurement of IgM. IgG, and IgA Rheumatoid Factors: High Sensitivity, Specificity, and Predictive Value for Rheumatoid Arthritis," The Journal of Rheumatology 1997: 24:61037-1044.

Tijssen, P., "Practice and Theory of Enzyme Immunoassays," eds. R.H. Burdon and v.P.H. Knippenberg, Elsevier, Amsterdam, 1990, pp. 221-278.

Van Der Heijde, D., "Joint Erosions and Patients with Early Rheumatoid Arthritis," British Journal of Rheumatology 1995; 34(suppl. 2) 74-78.

Waaler, E., "On the Occurrence of a Factor in Human Serum Activating the Specific Agglutination of Sheep Sheep Blood Corpuscles," Acta Pathol. Microbiol. Scand. 172-188, 1940.

Zweig, M. et al., "Receiver-Operating Characteristic (ROC) Plots: A Fundamental Evaluation Tool in Clinical Medicine," Clin. Chem. 39/4, 561-577 (1993).

* cited by examiner

ASSESSING RHEUMATOID ARTHRITIS BY MEASURING ANTI-CCP AND INTERLEUKIN 6

RELATED APPLICATIONS

This application is a continuation of PCT/EP2004/014527 filed Dec. 21, 2004, which claims priority to EP 03029658.6 filed Dec. 23, 2003.

FIELD OF THE INVENTION

The present invention relates to a method aiding in the assessment of rheumatoid arthritis. The method especially is used in assessing the absence or presence of rheumatoid arthritis in vitro. The method is for example practiced by analyzing biochemical markers, comprising measuring in a sample the concentration of anti-CCP and interleukin 6 and correlating the concentrations determined to the absence or presence of rheumatoid arthritis.

BACKGROUND OF THE INVENTION

The present invention relates to a method aiding in the assessment of rheumatoid arthritis. The method especially is used in assessing the absence or presence of rheumatoid arthritis in vitro. The method is for example practiced by analyzing biochemical markers, comprising measuring in a sample the concentration of anti-CCP and interleukin 6 and correlating the concentrations determined to the absence or presence of rheumatoid arthritis. To further improve the assessment of RA in a method of this invention the level of one or more additional marker may be determined together with anti-CCP and interleukin 6 and be correlated to the absence or presence of RA. The invention also relates to the use of a marker panel comprising anti-CCP and interleukin 6 in the diagnosis of rheumatoid arthritis and it teaches a kit for performing the method of the invention.

Rheumatoid arthritis ("RA") is a chronic, inflammatory, systemic disease that produces its most prominent manifestations in affected joints, particularly those of the hands and feet. The onset of rheumatoid arthritis can occur slowly, ranging from a few weeks to a few months, or the condition can surface rapidly in an acute manner.

RA has a worldwide distribution and involves all ethnic groups. Although the disease can occur at any age, the prevalence increases with age and the peak incidence is between the fourth and sixth decade. The prevalence estimates for the North American population vary from 0.3% to 1.5%. Today, over 2,500,000 individuals are diagnosed with rheumatoid arthritis in the United States alone, with some statistics indicating from 6.5 to 8 million potentially afflicted with the disease. Women are affected 2-3 times more often than men.

The early symptoms of rheumatoid arthritis are mostly joint specific such as painful joints with joint swelling or tenderness, but may also include rather non-specific manifestations like stiffness, fever, subcutaneous nodules, and fatigue. Very characteristic is the symmetric involvement of joints. The joints of the hands, feet, knees and wrists are most commonly affected, with eventual involvement of the hips, elbows and shoulders. As the disease progresses, any type of motion becomes very painful and difficult leading eventually to a loss of function of the involved joints The more severe cases of rheumatoid arthritis can lead to intense pain and joint destruction. Some 300,000 bone and joint replacement surgical procedures are performed annually in an effort to alleviate the pain and mobility loss resultant from arthritis related joint destruction.

The most widely used system to classify RA is the American College of Rheumatology 1987 revised criteria for the classification of RA. (Arnett, F. C., et al., Arthritis Rheum. 31 (1988) 315-324. According to these criteria (known as ARA-criteria), a patient is said to have RA if the patient satisfies at least four of the following seven criteria, wherein criteria 1-4 must be present for at least six weeks: 1) morning stiffness for at least one hour, 2) arthritis of three or more joint areas, 3) arthritis of hand joints, 4) symmetrical arthritis, 5) rheumatoid nodules, 6) serum rheumatoid factor ("RF"), and 7) radiographic changes. These criteria have a sensitivity and specificity of approximately 90%.

The only biochemical marker generally accepted (see the above ARA-criteria) and aiding in the diagnosis of RA is the rheumatoid factor (RF) as detected in serum.

The histological changes in RA are not disease-specific but largely depend on the organ involved. The primary inflammatory joint lesion involves the synovium. The earliest changes are injury to the synovial microvasculature with occlusion of the lumen, swelling of endothelial cells, and gaps between endothelial cells, as documented by electron microscopy. This stage is usually associated with mild proliferation of the superficial lining cell layer. Two cell types constitute the synovial lining: bone marrow derived type A synoviocyte, which has macrophage features, and mesenchymal type B synoviocyte. Both cell types contribute to synovial hyperplasia, suggesting a paracrine interaction between these two cell types. This stage of inflammation is associated with congestion, oedema, and fibrin exudation. Cellular infiltration occurs in early disease and initially consists mainly of T lymphocytes. As a consequence of inflammation, the synovium becomes hypertrophic from the proliferation of blood vessels and synovial fibroblasts and from multiplication and enlargement of the synovial lining layers. Granulation tissue extends to the cartilage and is known as pannus. The tissue actively invades and destroys the periarticular bone and cartilage at the margin between synovium and bone, known as erosive RA.

The articular manifestations of RA can be placed in two categories: reversible signs and symptoms related to inflammatory synovitis and irreversible structural damage caused by synovitis. This concept is useful not only for staging disease and determining prognosis but also for selecting medical or surgical treatment. Structural damage in the typical patient usually begins sometime between the first and second year of the disease (Van der Heijde, D. M., et al., Br. J. Rheumatol. 34 (1995) 74-78). Although synovitis tends to follow a fluctuating pattern, structural damage progresses as a linear function of the amount of prior synovitis.

The aetiology of the early events in RA remains elusive. An autoimmune component is widely accepted today but other factors are still disputed. The possibility of a bacterial or viral infection has been vigorously pursued. All efforts to associate an infectious agent with RA by isolation, electron microscopy, or molecular biology have failed. It is possible that there is no single primary cause of RA and that different mechanisms may lead to the initial tissue injury and precipitate synovial inflammation.

Clinical signs of synovitis may be subtle and are often subjective. Warm, swollen, obviously inflamed joints are usually seen only in the most active phases of inflammatory synovitis. Cartilage loss and erosion of periarticular bone are the characteristic features of structural damage. The clinical features related to structural damage are marked by progressive deterioration functionally and anatomically. Structural damage to the joint is irreversible and additive.

The effective treatment of rheumatoid arthritis has generally comprised a combination of medication, exercise, rest and proper joint protection therapy. The therapy for a particular patient depends on the severity of the disease and the joints that are involved. Non-steroidal anti-inflammatory drugs, corticosteroids, gold salts, methotrexate and systemic immunosuppressants are widely used to reduce inflammation and joint destruction. The use of steroids and immunosuppressants, however, has significant risks and side effects both in terms of toxicity and vulnerability to potentially lethal conditions. More recently therapeutics based on "biologicals" have been introduced into RA-therapy. Such therapeutics, e.g., are soluble receptors or antibodies directed against TNF-α that significantly reduce inflammation. Though very promising, biologicals are still in limited use due to high costs.

Data from longitudinal clinical and epidemiologic studies provide guidelines for treatment. These studies emphasize 1) the need for early diagnosis, 2) identification of prognostic factors, and 3) early aggressive treatment. Earlier diagnosis and treatment, preferably within the first several months after onset of symptoms, may help prevent irreversible joint damage.

Hence a need for methods, especially based on biochemical parameters, aiding in the assessment of rheumatoid arthritis exists. The present invention provides such methods and reagents for assessing the absence or presence of rheumatoid arthritis in vitro. The methods will also aid in monitoring the efficacy of treatment in patients suffering from RA.

SUMMARY OF THE INVENTION

The present invention is directed to a method for assessing rheumatoid arthritis in vitro by biochemical markers, comprising measuring in a sample the concentration of anti-CCP and interleukin 6 and correlating the concentrations determined to the absence or presence of rheumatoid arthritis.

The present invention also relates to the use of a marker panel comprising at least anti-CCP and interleukin 6 in the diagnosis of RA.

The present invention also provides a kit for performing the method according to the present invention comprising at least the reagents required to specifically measure anti-CCP and interleukin 6, respectively, and optionally auxiliary reagents for performing the measurement.

In a first preferred embodiment the present invention relates to a method for assessing rheumatoid arthritis in vitro by biochemical markers, comprising measuring in a sample the concentration of anti-CCP and interleukin 6 and correlating the concentrations determined to the absence or presence of rheumatoid arthritis.

BRIEF DESCRIPTION OF THE DRAWINGS

"RD-Score" in all figures stands for "regularized discriminant score", i.e., the score obtained by applying Regularized Discriminant Analysis; "AUC" in all figures stands for "area under the curve".

DETAILED DESCRIPTION OF THE INVENTION

Figure 1:
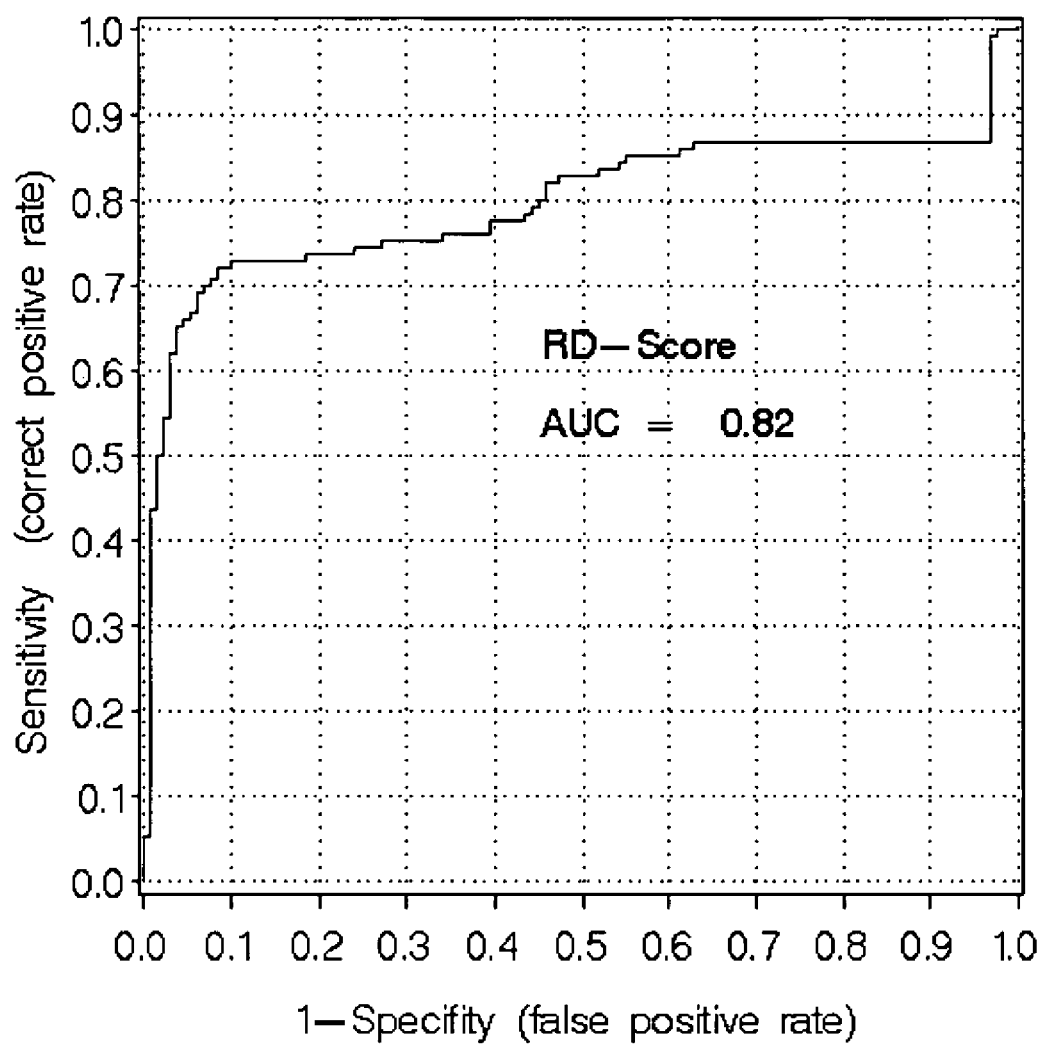
FIG. 1 is a graph showing ROC-analysis of patients diagnosed with RA versus Controls incl. OA using log total RF alone.

As used herein, each of the following terms has the meaning associated with it in this section.

The articles "a" and "an" are used herein to refer to one or to more than one (i.e. to at least one) of the grammatical object of the article. By way of example, "a marker" means one marker or more than one marker.

The term "marker" or "biochemical marker" as used herein refers to a molecule to be used as a target for analyzing patient test samples. Examples of such molecular targets are proteins or polypeptides themselves as well as antibodies present in a sample. Proteins or polypeptides used as a marker in the present invention are contemplated to include any variants of said protein as well as fragments of said protein or said variant, in particular, immunologically detectable fragments. One of skill in the art would recognize that proteins which are released by cells or present in the extracellular matrix which become damaged, e.g., during inflammation could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but differ in their PI or MW, or both (e.g., as a result of alternative mRNA or pre-mRNA processing, e.g. alternative splicing or limited proteolysis) and in addition, or in the alternative, may arise from differential post-translational modification (e.g., glycosylation, acylation, and/or phosphorylation).

The term marker as indicated above according to the present invention also relates to antibodies present in a sample. In the case of RA these antibodies are autoantibodies, i.e. antibodies in a patient sample which bind to an antigen present in or on or produced by the patient's own cells.

The term "sample" as used herein refers to a biological sample obtained for the purpose of evaluation in vitro. In the methods of the present invention, the sample or patient sample preferably may comprise any body fluid. Preferred test samples include blood, serum, plasma, urine, saliva, and synovial fluid. Preferred samples are whole blood, serum, plasma or synovial fluid, with plasma or serum being most preferred.

As the skilled artisan will appreciate, any such diagnosis is made in vitro. The patient sample is discarded afterwards. The patient sample is merely used for the in vitro diagnostic method of the invention and the material of the patient sample is not transferred back into the patient's body. Typically, the sample is a liquid sample.

The term "assessing rheumatoid arthritis" is used to indicate that the method according to the present invention will (together with other variables, e.g., the criteria set forth by the ARA (see above)) aid the physician to establish his diagnosis of RA. In a preferred embodiment this assessment will relate to the presence or absence of RA. As the skilled artisan will appreciate no biochemical marker is diagnostic with 100% specificity and at the same time 100% sensitivity for a given disease, rather biochemical markers are used to assess with a certain likelihood or predictive value the presence or absence of a disease. Preferably the method according to the present invention aids in assessing the presence or absence of RA.

As the skilled artisan will appreciate the step of correlating a marker level to the presence or absence of RA can be performed and achieved in different ways. In general a reference population is selected and a normal range established. It is no more than routine experimentation, to establish the normal range for both anti-CCP as well as IL-6 using an appropriate reference population. It is generally accepted that the normal range to a certain but limited extent depends on the reference population in which it is established. The ideal reference population is high in number, e.g., hundreds to thousands and matched for age, gender and optionally other variables of interest. The normal range in terms of absolute values, like a concentration given, also depends on the assay employed and the standardization used in producing the assay.

The levels given for anti-CCP and IL-6 in the examples section have been measured and established with the assay procedures given. It has to be understood that different assays may lead to different cut-off values, without departing from the scope of the present invention.

Citrullinated peptides are antigens for rather important autoantibodies as found in the sera of patients with RA. They have been intensively studied during the past years by several groups of researchers (cf. e.g., WO 98/08946; WO 98/22503; WO 99/28344; WO 99/35167, WO 01/46222, and WO 03/050542). Recently Schellekens and co-workers (Schellekens, G. A., Arthritis Rheum. 43 (2000) 155-163) reported that an ELISA-test based on specific cyclic citrullinated peptides (CCP) showed superior performance characteristics with regard to diagnostic accuracy for RA as compared to the same assay using linear peptides.

Auto-antibodies against CCP, i.e., antibodies which most likely are reactive with citrullinated polypeptides circulating in a patient serum and which bind to CCP in an in vitro assay are termed "anti-CCP". The patent application of van Venroji et al. (WO 98/22503) describes certain citrullinated peptides and shows that cyclization leads to an improved reactivity of the respective peptides. In a specific example it is shown that, if a peptide of the general formula HQCHQESTXGRSR-GRCGRSGS (SEQ ID NO: 1), where X stands for citrulline, is cyclisized by a disulfide bond between the two cysteine residues, the sensitivity is increased to 63% as compared to 36% to the corresponding linear peptide. As autoantibodies in patient sera have slightly different reactivity to different cyclic peptides a combination of peptides was suggested in WO 98/22503 to further improve the assay.

In a preferred embodiment anti-CCP is measured as described by van Venroij et al in WO 03/050542. In brief, a combination of peptides that contain epitope sites with the general formula X-G and X-nonG wherein X stands for citrulline, G for glycine and nonG for any of the amino acids H, I, W, S, R, K, Y, M, F, V, P, Cit or an analogue thereof is used to assess the level of anti-CCP antibodies (anti-CCP) in a sample. Specific peptides useful in such assessment are disclosed in WO 03/050542. As the skilled artisan will readily appreciate, further improvements and refinements regarding the cyclic citrullinated peptide antigen used in an assay to measure anti-CCP are possible which will e.g. result in an altered sequence of the cyclic citrullinated peptide sequence. However, such modifications will not depart from the spirit of this invention.

The antibody binding to CCP, i.e., anti-CCP, is measured in a serological assay. Preferably such assay is set up by using one or more CCP as antigen and detecting the binding of anti-CCP antibodies comprised in a sample to the CCP antigen by appropriate means.

Preferred means of detection are specific binding assays, especially immunoassays. Immunoassays are well known to the skilled artisan. Methods for carrying out such assays as well as practical applications and procedures are summarized in related textbooks. Examples of related textbooks are Tijssen, P., In: Practice and theory of enzyme immunoassays, eds. R. H. Burdon and v. P. H. Knippenberg, Elsevier, Amsterdam, 1990, 221-278 and various volumes of Methods in Enzymology, eds. S. P. Colowick, N. O. Caplan and S. P., Academic Press, dealing with immunological detection methods, especially volumes 70, 73, 74, 84, 92 and 121.

Anti-CCP antibodies may be detected by homogeneous assays formats, e.g., by agglutination of latex particles coated with CCP.

Preferably a heterogeneous immunoassay is used to measure anti-CCP. Such heterogeneous measurement is based on directly or indirectly coating CCP to a solid phase, incubating the solid phase with a sample known or suspected to comprise anti-CCP antibodies under conditions allowing for binding of anti-CCP antibodies to CCP, and directly or indirectly detecting the anti-CCP antibody bound. A further assay format is the so-called double antigen bridge assay, wherein, in case of an anti-CCP measurement, CCPs are used both at the solid phase side as well as at the detection side of this immunoassay and the autoantibodies in a patient sample form a bridge between these "double" antigens. Where necessary or appropriate, washing steps are included while performing a heterogeneous immunoassay.

Interleukin-6 (IL-6) is a 21 kDa secreted protein that has numerous biological activities that can be divided into those involved in hematopoiesis and into those involved in the activation of the innate immune response. IL-6 is an acute-phase reactant and stimulates the synthesis of a variety of proteins, including adhesion molecules. Its major function is to mediate the acute phase production of hepatic proteins, and its synthesis is induced by the cytokines IL-1 and TNF-α. IL-6 is normally produced by macrophages and T lymphocytes. The normal serum concentration of IL-6 is <5 pg/ml.

Whereas for anti-CCP the (auto-)antibodies as comprised in a sample are measured, for 1L-6 it is the marker molecule IL-6 itself, which is detected. IL-6 for example can be measured by a competitive type or a sandwich type immunoassay. IL-6 preferably is measured in a sandwich immunoassay which is essentially based on an antibody specifically binding to IL-6 which is directly or indirectly bound or capable of binding to a solid phase, an antibody specifically binding to IL-6 which is detectably labeled, and incubating these reagents under conditions allowing for binding of the anti-IL-6 antibodies to IL-6 in a sample, separating unbound detectably labeled antibody, determining the amount of labeled antibody bound via IL-6, and correlating the amount of labeled antibody bound to the concentration of IL-6 in the sample.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case for RA. Therefore, generally various clinical symptoms and biological markers are considered together for diagnosis of RA.

Markers can either be determined individually or in a preferred embodiment of the invention they can be measured simultaneously using a chip or a bead based array technology. The concentrations of the biomarkers are then interpreted independently using an individual cut-off for each marker or they are combined for interpretation.

As shown in the Examples section the mere combination of the two markers anti-CCP and IL-6 significantly improves the diagnostic accuracy for RA.

In a method according to the present invention at least the concentration of the biomarkers and IL-6, respectively, is determined and the marker combination is correlated to the absence or presence of RA.

As the skilled artisan will appreciate there are many ways to use the measurements of two or more markers in order to improve the diagnostic question under investigation. In a quite simple, but nonetheless often effective approach, a positive result is assumed if a sample is positive for at least one of the markers investigated. This may e.g. the case when diagnosing an infectious disease, like AIDS. Frequently, however, the combination of markers is evaluated. Preferably the values measured for markers of a marker panel, e.g. for anti-CCP and IL-6, are mathematically combined and the combined value is correlated to the underlying diagnostic question. Marker values may be combined by any appropriate state of the art mathematical method. Well-known mathematical methods for correlating a marker combination to a disease employ methods like, Discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. The skilled artisan will have no problem in selecting an appropriate method to evaluate a marker combination of the present invention. Preferably the method used in correlating the marker combination of the invention e.g. to the absence or presence of RA is selected from DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression). Details relating to these statistical methods are found in the following references: Ruczinski, I., Kooperberg C., LeBlanc, M., Logic regression, J. of Computational and Graphical Statistics, 12 (2003) 475-511; Friedman, J. H., Regularized Discriminant Analysis, J. of the American Statistical Association, 84 (1989) 165-175; Trevor Hastie, Robert Tibshirani and Jerome Friedmann, The Elements of Statistical Learning, Springer Verlag, 2001; Breiman, L., Friedman, J. H., Olshen, R. A., Stone, C. J. (1984) Classification and regression trees, California: Wadsworth; Breiman, L., Random Forests, Machine Learning, 45 (2001) 5-32; Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

It is a preferred embodiment of the invention to use an optimized multivariate cut-off for the underlying combination of biological markers and to discriminate state A from state B, e.g. diseased from healthy. In this type of analysis the markers are no longer independent but form a marker panel. It could be established that combining the measurements of anti-CCP and of IL-6 does significantly improve the diagnostic accuracy for RA as compared to either healthy controls or, as also assessed, as compared to patients with osteoarthritis (OA). Especially the later finding is of great importance, because patients with OA and RA, respectively, may require quite different treatments.

Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability, to correctly distinguish two different conditions of the subjects investigated. Such conditions are for example health and disease or benign versus malignant disease.

In each case, the ROC plot depicts the overlap between the two distributions by plotting the sensitivity versus 1−specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1−specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always $\geq 0.5$ (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

In a preferred embodiment the present invention relates to a method for improving the diagnostic accuracy for rheumatoid arthritis versus healthy controls and/or patients suffering from OA by measuring in a sample the concentration of at least anti-CCP and interleukin 6 and correlating the concentrations determined to the presence or absence of rheumatoid arthritis, the improvement resulting in more patients being correctly classified as suffering from RA versus healthy controls and/or patients suffering from OA as compared to a classification based on anti-CCP alone. The RA marker panel comprising anti-CCP and IL-6 can of course also be used in assessing the severity of disease for patients suffering from RA.

As the skilled artisan will appreciate one or more additional biomarker may be used to further improve the assessment of RA. To illustrate this additional potential of using anti-CCP and IL-6 as the key markers of a panel of markers for assessment of RA the term "at least" has been used in the appending claims. With other words, the level measured for one or more additional marker may be combined with the measurement of anti-CCP and IL-6 in the assessment of RA.

The one or more additional marker used together with anti-CCP and IL-6 may be considered to be part of an RA marker panel, i.e., a series of markers appropriate to further refine the assessment of RA. The total number of markers in an RA marker panel is preferably less than 20 markers, more preferred less than 15 markers, also preferred are less than 10 markers with 8 or less markers being even more preferred. Preferred are RA marker panels comprising 3, 4, 5, or 6 markers in total.

In a preferred embodiment the present invention thus relates to a method for assessing the absence or presence of rheumatoid arthritis in vitro by biochemical markers, comprising measuring in a sample the concentration of anti-CCP, interleukin 6 and in addition the concentration of one or more other marker and correlating the concentrations of anti-CCP, IL-6 and of the one or more additional marker to the absence or presence of rheumatoid arthritis.

It will be appreciated that the one or more other marker may be combined with any known or future marker of RA. A marker does qualify as an RA marker if the AUC for this marker alone, when assessing the diagnostic accuracy by comparing patients with RA to healthy controls, is at least 0.65.

Preferably the one or more other marker is selected from the group consisting of C-reactive protein (CRP), serum amyloid A (SAA), S100, osteopontin, RF, matrix metalloprotease 1 (MMP-1), matrix metalloprotease 3 (MMP-3), hyaluronic acid, sCD14, angiogenesis markers and products of bone, cartilage or synovium metabolism.

C-reactive protein (CRP) is a homopentameric $Ca^{2+}$-binding acute phase protein with 21 kDa subunits that is involved in host defense. CRP synthesis is induced by IL-6, and indirectly by IL-1, since IL-1 can trigger the synthesis of IL-6 by Kupffer cells in the hepatic sinusoids. The normal plasma concentration of CRP is <3 µg/ml (30 nM) in 90% of the healthy population, and <10 µg/ml (100 nM) in 99% of healthy individuals. Plasma CRP concentrations can, e.g. be measured by homogeneous assay formats or ELISA. C-reactive protein is a marker for underlying systemic inflammation.

Serum amyloid A (SAA) is an acute phase protein of low molecular weight of 11.7 kDa. It is predominantly synthesized by the liver in response to IL-1, IL-6 or TNF-α stimulation and is involved in the regulation of the T-cell dependent immune response. Upon acute events the concentration of SAA increases up to 1000-fold reaching one milligram per milliliter. It is used to monitor inflammation in diseases as divers as cystic fibrosis, renal graft refection, trauma or infections. In rheumatoid arthritis is has in certain cases been used as a substitute for CRP, but, SAA is not yet as widely accepted.

Osteopontin (OPN) is a secreted, highly acidic, calcium-binding, phosphorylated glycoprotein. Three isoforms are known that originate from alternative splicing which are either free or bound to the extracellular matrix. Through a RDG-motif of the 32 kDa-peptide backbone OPN can bind to integrins such as avβ3. Though it was originally purified from bone matrix it is expressed in numerous body fluids and tissues including milk, urine, activated T-cells, macrophages, fibroblasts, smooth muscle cells, kidney tissue and some tumor cells. Its expression is stimulated in response to several cytokines, growth factors or inflammatory mediators. Increased OPN concentrations have been associated with sepsis, metastatic cancer, cerebral ischemia, atherosclerotic plaques, granuloma formation in tuberculosis and autoimmune diseases such as multiple sclerosis (Chabas, D., et al., Science 294 (2001) 1731-1735) or RA (Petrow, P. K., et al., Arthritis Rheum. 43 (2000) 1597-1605).

Rheumatoid factors (RF) are autoantibodies directed against the constant Fc-region of immunoglobulin G molecules (Waaler, E., Acta Pathol. Microbiol. Scand. 17 (1940) 172-188; Moore, T. L., and Dorner, R. N., Clin. Biochem. 26 (1993) 75-84). Though RF has some limitations it is currently the only immunologic marker of rheumatoid arthritis included in the ARA-criteria. Besides of RA it is also found in other inflammatory rheumatic diseases, non-rheumatic disease and even in healthy persons aged over 60 years (Bartfeld, H., Ann. NY Acad. Sci. 168 (1969) 30-40). RF autoantibodies belong to all immunoglobulin classes and most of the assays used today do not differentiate between the isotypes IgM, IgG and IgA. These RF-assays also termed total-RF assays determine mostly IgM but also cover IgG or IgA to some degree depending on the assay format and the supplier (Bas, S., et al., Ann. Rheum. Dis. 61 (2002) 505-510). More recently the RF-isotypes IgG and IgA have come into focus for the diagnosis of RA. When all three RF-isotypes are elevated the diagnostic value of the RF-assay might be improved (Swedler, W., et al., J. Rheumatol 24 (1997) 1037-1044). Additionally some prognostic value has been ascribed to certain of these RF-isotypes. Especially, a high concentration of IgA-type RF was found to be an indicator for severe disease progression (Jorgensen, C., et al., Clin. Exp. Rheum. 14 (1996) 301-304). In a marker combination according to the present invention the marker RF can be any form of RF-determination including total RF, single specific RF-isotypes or any combination of RF-isotypes.

The family of matrix-metalloproteinases (MMPs) degrades almost all components of the extra-cellular matrix. Hence MMPs have been related to various types of cancer but also to inflammatory processes in RA. MMP-1 and MMP-3 are produced by fibroblasts, osteoblasts and endothelial cells upon stimulation by pro-inflammatory cytokines like IL-1 or TNF-α. Generally MMPs are found in the circulation as inactive pro-form and the marker MMP-1 and MMP-3, respectively, as used herein also relates to such inactive pro-form. MMP-1 and MMP-3 have been detected in synovial fluid of RA-patients and the levels are responsive to anti-TNF-α therapy. The most preferred metalloprotease to be used in an RA marker panel according to the present invention is MMP-1.

Instead of the metalloproteinases mentioned above it is also possible to used their corresponding inhibitors collectively referred to as tissue inhibitors of matrix metalloproteinases (TIMPs), eg. MMP-1 and MMP-3 are in vivo inactivated by TIMP-1 a sialoglycoprotein of 29.5 kD that forms a 1:1 stoichiometric complex with the MMPs. The relation of TIMP-1 and TIMP-2 to the destruction of cartilage has been investigated in RA (Ishiguro, N., et al., Arthritis Rheum. 44 (2001) 2503-2511).

S100-proteins form a constantly increasing family of $Ca^{2+}$-binding proteins that today includes more than 20 members. The physiologically relevant structure of S100-proteins is a homodimer but some can also form heterodimers with each other, e.g. S100A8 and S100A9. The intracellular functions range from regulation of protein phosphorylation, of enzyme activities, or of the dynamics of the cytoskeleton to involvement in cell proliferation and differentiation. As some S100-proteins are also released from cells, extracellular functions have been described as well, e.g., neuronal survival, astrocyte proliferation, induction of apoptosis and regulation of inflammatory processes. S100A8, S100A9, the heterodimer S100A8/A9 and S100A12 have been found in inflammation with S100A8 responding to chronic inflammation, while S100A9, S100A8/A9 and S100A12 are increased in acute inflammation. S100A8, S100A9, S100A8/A9 and S100A12 have been linked to different diseases with inflammatory components including some cancers, renal allocraft rejection, colitis and most importantly to RA. (Burmeister, G., and Gallacchi, G., Inflammopharmacology 3 (1995) 221-230; Foell, D., et al., Rheumathology 42 (2003) 1383-1389). The most preferred S100 markers for use in an RA marker panel according to the present invention are S100A8, S100A9, S100A8/A9 heterodimer and S100A12.

CD14 is a membrane protein of promonocytes, monocytes, macrophages, and activated granulocytes where it serves as a receptor for lipopolysaccharide. It induces the secretion of cytotoxic and immunomodulating factors like reactive oxygen ($O_2$), tumor necrosis factor (TNF-α), interleukins (IL-1, IL-6 and IL-8) and platelet-activating factor (PAF). Membrane bound CD14 is shed to give soluble CD14 (sCD14) in response to activating or differentiating factors such as IFNγ or TNF-α. The physiological function of sCD14 is not yet entirely clear. Since inflammatory and immune processes are involved in RA and other autoimmune diseases, sCD14 was also investigated in such diseases. When anti-CD14 therapy was evaluated as a new therapeutic option in RA previously elevated concentrations of sCD14 rapidly decreased and synovitis was reduced (Horneff, G., et al., Clin. Exp. Immunol 91 (1993) 207-213).

The glycosaminoglycan hyaluronic acid is one of the macromolecules essential for the function of a joint. It is synthesized by fibroblasts and other specialized connective tissue cells. Hyaluronic acid is involved in formation of the extracellular matrix and in cell to cell contacts. High concentrations are found in synovial fluid where it is responsible for the retention of water thereby contributing to the lubrication of joints. In rheumatoid arthritis the synthesis of hyaluronic acid is stimulated by the proinflammatory mediators IL-1 and TNF-α leading to increase serum/plasma levels (Sawai, T., and Uzuki, M., Connective Tissue 33 (2001) 253-259).

A feature of rheumatoid arthritis is the invasion of joints with proliferating synovial tissue also known as pannus. A significant part of the pannus consists of blood vessels that supplies nutrients to the growing tissue. Therefore, molecules relevant in angiogenesis have been investigated in RA also, both as RA markers but also as therapeutic targets (Brenchley, P. E. C., Clin. Exp. Immunol. 121 (2000) 426-429). Amongst these, the vascular endothelial growth factor (VEGF) has been evaluated in more detail. VEGF is a secreted glycoprotein that is spliced to four different isoforms. Two of these isoforms are readily diffusible while the remaining isoforms bind tightly to heparin and are mostly found in association with heparin containing proteoglycans. VEGF acts as a chemokine on endothelial cells, monocytes and osteoblasts ultimately leading to neovascularization and increased microvascular permeability. VEGF has been detected in synovial fluid and serum of RA patients (Lee, S. S., et al., Clin. Exp. Rheumathology 19 (2001) 321-324; Ballara, S., Arthritis Rheum. 44 (2001) 2055-2064). Preferably, the marker of angiogenesis is VEGF.

The most prominent joint tissues are bone, cartilage and the synovium. Since rheumatoid arthritis is a destructive disease these tissues will be most affected. They are a likely source of potential biological markers in the field of RA. In principle these markers may come not only from the destruction of the respective tissue but also from a deregulated and/or ineffective repair process. The experienced artisan will understand that markers of bone, cartilage or synovium metabolism can originate either from. synthesis or from destruction of these tissues. The various markers of bone, cartilage and/or synovium metabolism can be delineated from two different groups of proteins. They come either from the numerous types of collagen or from non-collagenous proteins. Non-collagenous proteins are often involved in the formation of the extracellular matrix. Some of these markers can be found in all three tissues in varying amounts.

Markers and products of bone and/or cartilage metabolism include both markers of bone and/or cartilage degradation as well as markers of bone and/or cartilage formation. Preferred markers derived from collagen metabolism are markers such as:

Pyridinoline (PYD), deoxy-pyridinoline (DPD) and Glc-Gal-PYD: Pyridinoline (PYD) stabilizes collagen by cross-linking the strands of the collagen triple helix. The chemical structure of PYD is very stable and can be found in serum and urine as an end product of collagen degradation (Knott, L., and Bailey, A. J., Bone 22 (1998) 181-187). It has been linked to arthritis (Kaufmann, J., et al., Rheumatology 42 (2003) 314-320). PYD monitors cartilage involvement of joint destruction since it is released from cartilage and only to some degree from bone while its close cousin deoxy-pyridinoline (DPD) originates mostly from bone. All three markers have been linked to arthritis (Kaufmann, supra). The glycosylated form Glc-Gal-PYD has mostly been found in synovial tissue (Gineyts, E., et al., Rheumatology 40 (2001) 315-323;

Cross-linked telopeptides: CTX-I, CTX-II, NTX-I and the LQ-epitope which are cross-linked telopeptides either from the C- or N-terminus of collagens type I or type II, respectively, and of which β-CTX-I is also known as β-CrossLaps® (Bonde, M., et al., Clin. Chem. 40 (1994) 2022-2025). Type I collagen carboxyterminal telopeptide (ICTP) refers to a fragment and marker of type I collagen which originally has been derived from type I collagen by cyanobromide cleavage;

Linear peptides derived from collagen: The assay termed Cartilaps® measures a linear peptide that is derived from the C-terminal region of collagen type I;

Modified amino acids: Collagen comprises modified amino acids like hydroxyproline and galactosyl hydroxylysine which may be used as a marker of collagen break-down (Al-Dehaimi, A. W., et al., Clin. Chem. 45 (1999) 676-681;

Collagen neoepitopes: Col2-¾ and CIIN are neoepitopes generated by the initial cleavage of collagen II by collagenases (Billinghurst, R. C., et al., J. Clin. Invest. 99 (1997) 1534-1545; and Collagen markers considered reflecting bone formation: The N-terminal as well as the C-terminal pro-peptide of type I collagen (PINP and PICP), respectively, are clipped from the precursor polypeptide (procollagen) during/after synthesis and considered markers of bone formation.

PIICP is the corresponding pro-peptide from collagen type II, whereas PIIINP is derived from collagen III.

Preferably the marker of bone and/or cartilage metabolism also my be a non-collagenous marker, like: CS846, which is a chondriotin sulfate epitope created during aggrecan synthesis; cartilage oligomeric matrix protein (COMP) that has bridging functions in cartilage (Saxne, T., and Heinegard, D., Br. J. Rheumatol. 31 (1992) 583-591); cartilage intermediate layer protein (CILP), which is a matrix protein of cartilage (Lorenzo, P., et al., J. Biol. Chem. 273 (1998) 23463-23468); cartilage matrix proteins 1-3 also known as matrilins; chondromodulins that act as signaling molecules in cartilage (Suzuki, F., Connect. Tissue Res. 35 (1996) 303-307); cartilage derived retinoic acid-sensitive protein (CD-RAP) or MIA, which has a yet to be defined function in chondrocyte modulation (Müller-Ladner, U., et al., Rheumatology 38 (1999) 148-154); osteocalcin, which is synthesized by osteoblasts, belongs to the major non-collagen matrix protein of bone and is used to monitor bone turnover (Gundberg, C. M., et al., J. Clin. Ligand Assay 21 (1998) 128-138); and the bone sialoproteins, which are major non-collagen matrix proteins of bone, such as bone sialoprotein II, now known as bone sialoprotein, which e.g., has been evaluated as marker for bone turn-over (Saxne, T., et al., Arthritis Rheum. 38 (1995) 82-90).

Products of metabolism within the synovium which may be used as a marker in assessing RA include: CTX-III, which is a telopeptide derived from collagen type III, YKL-40 the later being a chitinase 3 like protein of the extracellular matrix (Johansen, J. S., et al., Scand. J. Rheumatol. 30 (2001) 297-304), and aggrecan, which is a building block of proteoglycans as well as its degradation product keratan sulfate.

Preferably the RA marker panel comprises at least three markers, wherein anti-CCP, IL-6 and a third marker selected from the group consisting of CRP, SAA, S100, osteopontin, RF, MMP-1, MMP-3, hyaluronic acid, and a product of collagen metabolism are contained.

In the assessment of RA a marker panel comprising anti-CCP, IL-6 and S100, especially, S100A12 is preferred.

A further preferred panel of RA markers comprises anti-CCP, IL-6 and SAA.

A further preferred panel of RA markers comprises anti-CCP, IL-6 and the pro-form of MMP-1, i.e. pro-MMP-1.

As mentioned further above (see ARA criteria)—despite severe limitations—the rheumatoid factor (RF) currently is the only biochemical marker generally accepted to aid in establishing the diagnosis of RA. It is clearly expected that the marker combination of the present invention will significantly improve the diagnosis of RA and will supplement or might be even finally replace the RF assay. The use of a marker panel comprising at least anti-CCP and interleukin 6 in the diagnosis of RA therefore represents a further preferred embodiment of the present invention.

As the skilled artisan will appreciate one or more additional marker may be used to further improve the diagnostic accuracy, or, where required increase the diagnostic sensitivity at the expense of specificity or vice versa. In some diagnostic areas, e.g., in the detection of an HIV-infection sensitivity is of utmost importance. The high sensitivity required may be achieved at the expense of specificity, leading to an increased number of false positive cases. In other cases, e.g. as a simple example, when assessing blood group antigens, specificity is of paramount importance.

A further preferred embodiment relates to the use of a marker panel in the diagnosis of RA the panel comprising anti-CCP, interleukin 6 and at least one additional marker selected from the group consisting of CRP, SAA, S100, osteopontin, RF, MMP-1, MMP-3, hyaluronic acid, sCD14, angiogenesis markers and products of bone, cartilage or synovium metabolism.

The method according to the present invention will also be of great use in assessing the severity of RA. The higher the level of anti-CCP and/or the higher the level of IL-6 the more severe is the disease. With the marker combination or marker panels now at hand it will be no more than routine experimentation to develop e.g., disease scores as an indicator for severity of disease. The method according to the present invention thus is preferably also used to assess the severity of disease.

The method of the present invention will also be of great help in monitoring the course of disease. This is most easily achieved by measuring in a patient sample anti-CCP and IL-6 as well as optionally additional markers at various points in time and comparing the absolute and/or the relative levels of the markers at these different time points. It thus is further preferred to use the method according to the present invention to monitor the course of disease in a patient with RA.

It is also recognized that the present invention will be of great help in assessing the efficacy of any treatment for RA. The efficacy of treatment will be reflected by changes in the marker level. If a treatment has the desired effect at least one of the two marker levels of anti-CCP or IL-6 will decrease. The method according to the present invention thus preferably is also used to assess the efficacy of treatment. The same phenomenon, i.e. a reduction in marker level of at least one of anti-CCP or IL-6 can easily be applied for selection of the right drug as well as the most appropriate dosing of drugs in RA. The use of a method of this invention in selection of the right drug and/or the most appropriate dosing is also preferred.

The method of the present invention will also enable the selection and identification of new drugs in the field of RA. This application represents a further preferred embodiment.

It will also be a great advantage that sub-groups of patients can now be identified for and in clinical studies which differ in their level of anti-CCP and IL-6 and to correlate this difference in marker level to the efficacy of the drug under investigation.

The present invention also relates to a kit for performing the method of this invention comprising the reagents required to specifically measure anti-CCP and interleukin 6, respectively. The kit may optionally comprise auxiliary reagents for performing the measurement of both anti-CCP and IL-6.

The following examples and figures are provided to aid the understanding of the present invention, the true scope of which is set forth in the appended claims. It is understood that modifications can be made in the procedures set forth without departing from the spirit of the invention.

SPECIFIC EMBODIMENTS

Example 1

Study Population

Samples derived from 389 highly characterized RA patients with maximum disease duration of 15 years were collected in five European centers with a follow-up of two years. All individuals were diagnosed as RA-patients according to the ARA-criteria and had a functional status of $\leq$III as classified by the ARA classification criteria (Hochberg, M. C., et al., Arthritis Rheum. 35 (1992) 498-502). All patients were documented with an extensive case report form (CRF). The CRF included the Health Assessment Questionnaire, the SF36 Questionnaire, swollen and tender joint count, the Larsen Score, laboratory parameters, clinical history of relevant surgery, medication, co-morbidities and medication for co-morbidities. X-rays were taken every year following a standardized procedure. Only baseline samples obtained from the subjects included in this study were included in the present analysis.

Samples derived from 624 control subjects were collected as well. From these controls only RA-positive subjects but not other forms of arthritis were excluded. 200 samples were drawn from this cohort to age-match the RA-samples of the study. Since the focus of the study was to discriminate RA not only from healthy subjects but also from other joint diseases, 190 patients with either tibiofemoral or patellofemoral OA of the knee were added as disease controls. For these OA patients clinical and laboratory parameters were determined and radiographic Kellgren & Lawrence Score was calculated (Kellgren, J. H., and Lawrence, J. S., Ann. Rheum. Dis. 16 (1957) 494-502).

Demographic data for the study population are given in Table 1.

TABLE 1

Patient collectives

| Collective | N | Age | Gender (f/m/?) |
|---|---|---|---|
| RA | 389 | 59.1 (16-87) | 256/132/1 |
| Controls incl. OA | 390 | 60.6 (38-92) | 195/195/0 |

Example 2

Markers Measured

Table 2 presents a selection of the assays used and gives the test format as well as the suppliers of the assays. Most of the assays were manual microtiter plate format (MTP) ELISAs. RF and CRP were determined in a homogeneous test format on an automatic Hitachi analyzer. Marker concentrations were determined in serum samples with these commercially available assays for patients as well as for controls.

TABLE 2

Assays and Suppliers

| Biomarker | Assay type/format | Source |
|---|---|---|
| Anti-CCP | Sandwich ELISA, MTP | Axis-Shield, Dundee (UK) |
| CRP | Homogenous assay, Hitachi | Roche Diagnostics, Mannheim (FRG) |
| Hyaluronic acid | Sandwich ELISA, MTP | Chugai, Tokyo (J) |
| IL-6 | Sandwich ELISA, MTP | Roche Diagnostics, Mannheim (FRG) |
| RF | Homogenous assay, Hitachi | Roche Diagnostics, Mannheim (FRG) |
| SAA | Sandwich ELISA, MTP | Biosource, Nivelles (B) |

Example 3

Statistical Evaluation

The patient cohorts were randomly split in a training set (app. 67%) and in a test set (app. 33%). On the training set a classification algorithm was develop and on the independent test set the algorithm was validated. As can be seen in Table 3 the respective sets were closely matched in size as well as age.

TABLE 3

Age distribution of collectives

| Group | Study | N | Mean | Max | q3 | Median | q1 | Min |
|---|---|---|---|---|---|---|---|---|
| Training | RA | 259 | 58.7 | 87 | 68 | 59 | 51 | 23 |
| Training | Controls incl. OA | 261 | 60.2 | 92 | 69 | 60 | 51 | 42 |
| Test | RA | 130 | 59.8 | 83 | 68 | 61 | 52 | 16 |
| Test | Controls incl. OA | 129 | 61.3 | 84 | 70 | 63 | 52 | 38 |

The classification algorithms were generated with the Regularized Discriminant Analysis (RDA), which is a generalization of the common Discriminant Analysis, i.e. Quadratic- and Linear Discriminant Analysis (McLachlan, G. J., Discriminant Analysis and Statistical Pattern Recognition, Wiley Series in probability and mathematical statistics, 1992). In the RDA alternatives to the usual maximum likelihood (plug-in) estimates for the covariance matrices are used. These alternatives are characterized by two parameters ($\lambda, \gamma$), the values of which are customized to individual situations by jointly minimizing a sample-based estimate of future misclassification risk (Friedman, J. H., Regularized Discriminant Analysis, J. of the American Statistical Association, Vol. 84 (1989) 165-175). As an alternative method Support Vector Machines algorithms (Hastie, Trevor, Tibshirani, Robert, Friedman, Jerome, The Elements of Statistical Learning, Springer Series in Statistics, 2001) can be fitted with comparable. classification results.

The marker panels were stepwise constructed starting from the best single marker for the classification problem and ending when the total classification error do not change remarkable any more. In order to gain centralized distributions every single marker was transformed with the natural logarithmic function. 10-fold cross validation was used on the training set to get robust estimates of the total error (sensitivity, specificity). Once the marker panel was defined, it was validated without any further adjustment with an independent test set.

Example 4

Identification of a Marker Panel for the Diagnosis of RA

Table 4 presents the classification results of patients diagnosed with RA versus controls incl. OA on the training set. The first marker selected was anti-CCP, the second one IL-6 and the third and last one hyaluronic acid when the algorithm stopped. The classification results of the marker combination anti-CCP, IL-6 and SAA are reported too because it was bet only by a narrow margin by the combination anti-CCP, IL-6 and hyaluronic acid. As a reference the classification results for total RF are presented, which as mentioned above is currently the only biochemical marker forming part of the ARA-criteria.

The aim of the current invention was to improve the correct diagnosis of RA versus controls including OA. The diagnostic value of the identified marker panel is best reflected in Table 4 by the total error of the classification. RF, currently the single biological marker included in the ARA-criteria, gives a total error of 0.18. Anti-CCP as a single marker already reduces it to 0.14. The preferred combination of anti-CCP and IL 6 significantly improves the classification with a total error of 0.12. Adding a third marker finally helps to further minimize the misclassification. The marker panel anti-CCP, IL 6 plus hyaluronic acid has a total error of 0.11, and the combination of anti-CCP, IL 6 plus SAA is comparable giving a total error of 0.12.

TABLE 4

Classification results on the training set of patients diagnosed with RA versus controls incl. OA

| | | | Cross validation (10-fold) | | |
|---|---|---|---|---|---|
| No of Markers | Marker or marker panel | Method (RDA) | TOTAL ERROR | Correct pos. Sensitivity | Correct neg. Specificity |
| 1 | log total RF | $\lambda = 0, \gamma = 0$ | 0.184 | 68.2% | 95.6% |
| 1 | log anti-CCP | $\lambda = 0, \gamma = 0$ | 0.146 | 74.4% | 96.6% |
| 2 | log anti-CCP, log IL-6 | $\lambda = 0, \gamma = 0$ | 0.115 | 80.3% | 96.9% |
| 3 | log anti-CCP, log IL-6, log hyaluronic acid | $\lambda = 0, \gamma = 0$ | 0.108 | 82.1% | 96.5% |
| 3 | log anti-CCP, log IL-6, log SAA | $\lambda = 0, \gamma = 0.25$ | 0.117 | 80.3% | 96.6% |

5 clearly show that the combination of anti-CCP, IL 6 and optionally at least one additional marker significantly improves the diagnosis of RA.

TABLE 5

Classification results on the test set of patients diagnosed with RA versus controls including patients with OA

| | | | Classification of Test Set | | |
|---|---|---|---|---|---|
| No of Markers | Marker or marker panel | Method (RDA) | TOTAL ERROR | Correct pos. Sensitivity | Correct neg. Specificity |
| 1 | log total RF | $\lambda = 0, \gamma = 0$ | 0.193 | 66.9% | 94.6% |
| 1 | log anti-CCP | $\lambda = 0, \gamma = 0$ | 0.166 | 66.9% | 100% |
| 2 | log anti-CCP, log IL-6 | $\lambda = 0, \gamma = 0$ | 0.112 | 80% | 97.7% |
| 3 | log anti-CCP, log IL-6, log hyaluronic acid | $\lambda = 0, \gamma = 0$ | 0.108 | 80% | 98.5% |
| 3 | log anti-CCP, log IL-6, log SAA | $\lambda = 0, \gamma = 0.25$ | 0.100 | 80% | 100% |

Figure 2:
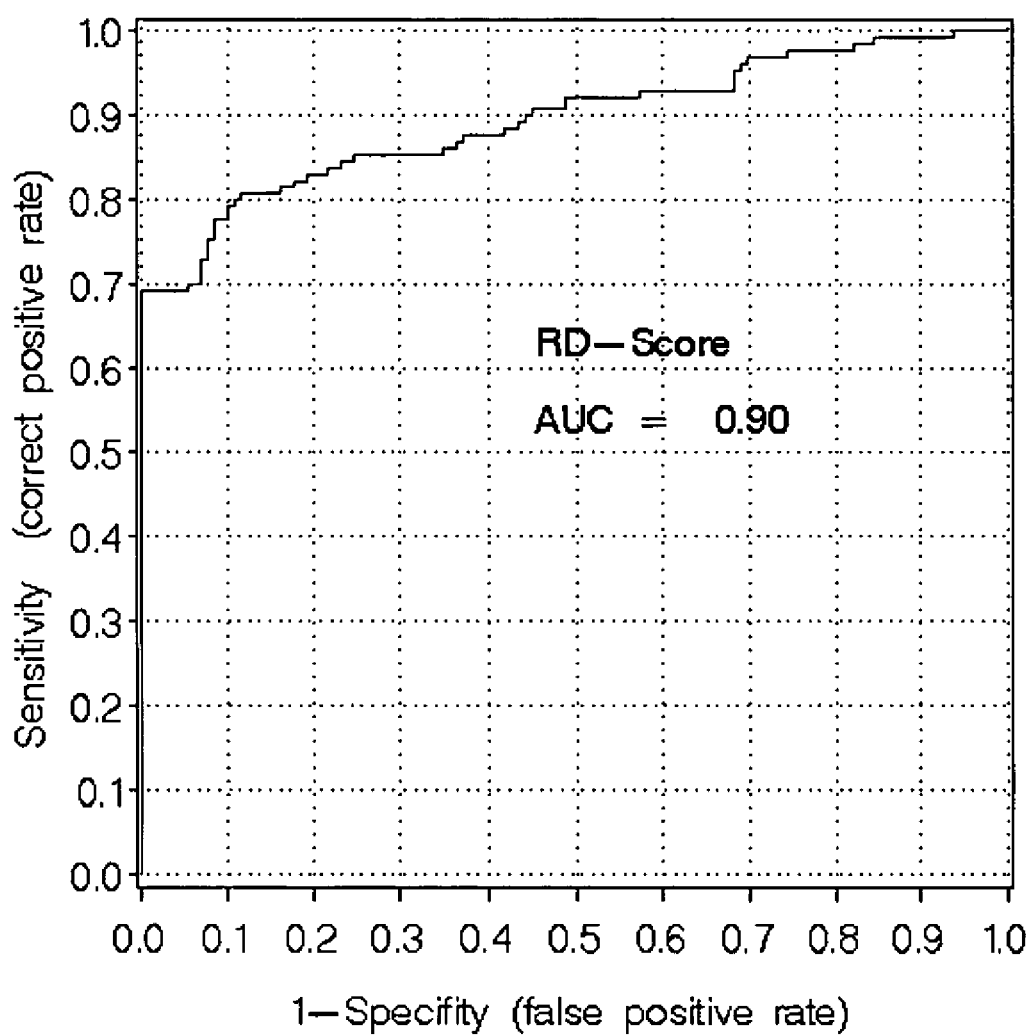
FIG. 2 is a graph showing ROC-analysis of patients diagnosed with RA versus Controls incl. OA using log anti-CCP alone.
Figure 3:
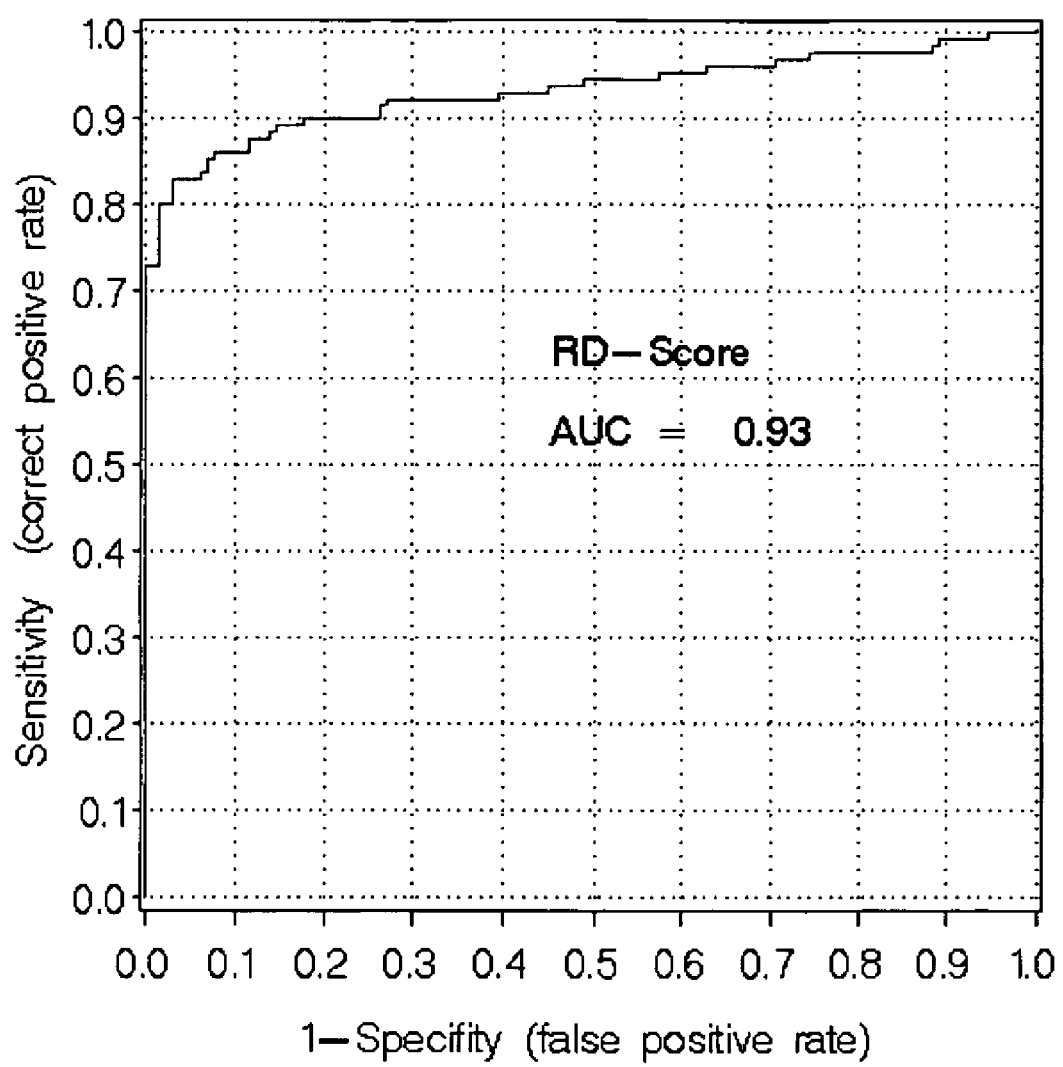
FIG. 3 is a graph showing ROC-analysis of patients diagnosed with RA versus Controls incl. OA using the combination log anti-CCP and log IL-6.
Figure 4:
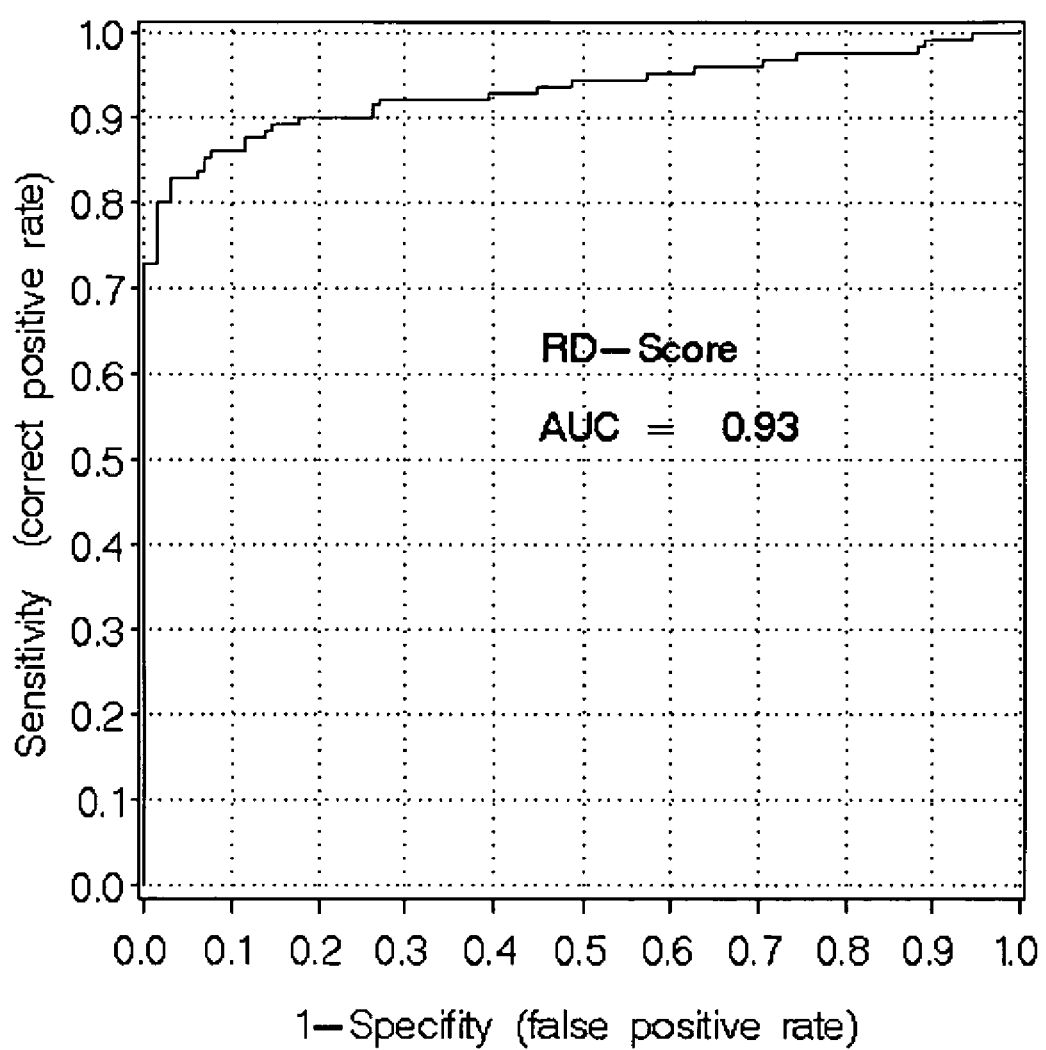
FIG. 4 is a graph showing ROC-analysis of patients diagnosed with RA versus Controls incl. OA using the combination log anti-CCP and log IL-6 and log hyaluronic acid.
Figure 5:
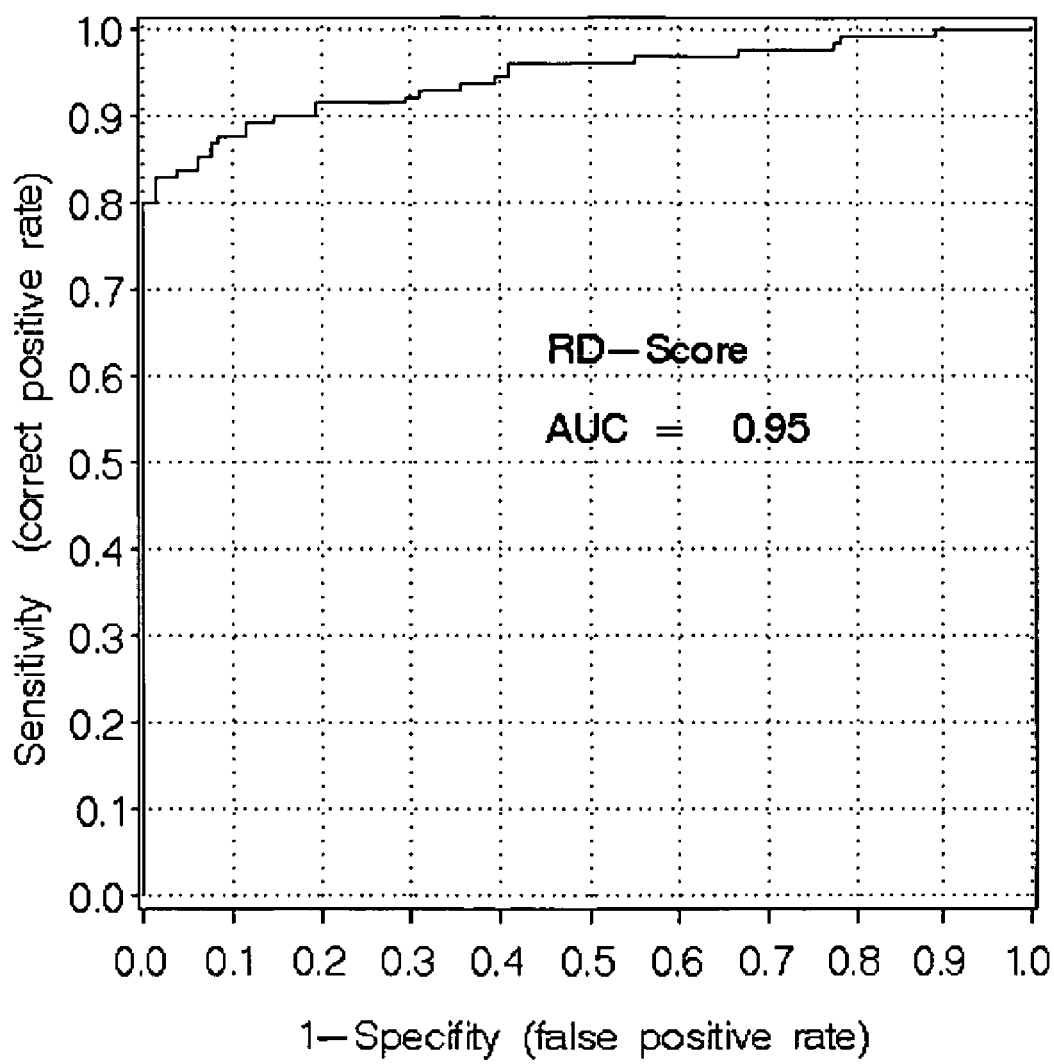
FIG. 5 is a graph showing ROC-analysis of patients diagnosed with RA versus Controls incl. OA using the combination of log anti-CCP and log IL-6 and log SAA.

The ROC-curves for the markers and marker combinations, respectively, of Table 5 are shown in FIGS. 1 to 5.

---

SEQUENCE LISTING

<160> NUMBER OF SEQ ID NOS: 1

<210> SEQ ID NO 1
<211> LENGTH: 21
<212> TYPE: PRT
<213> ORGANISM: Artificial sequence
<220> FEATURE:
<223> OTHER INFORMATION: synthetical peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 1

His Gln Cys His Gln Glu Ser Thr Xaa Gly Arg Ser Arg Gly Arg Cys
1               5                   10                  15

Gly Arg Ser Gly Ser
            20

---

Most critical for the approach chosen in this study is the question if it has a general applicability. To test this, the marker panel identified in the training set was validated with an independent test set. As the skilled artisan will understand, the results of the training and the test set may differ slightly because both sets were truly independent. Table 5 gives the classification results using the same single markers or marker panels as in Table 4. As in the training set the combination of anti-CCP, IL 6 and hyaluronic acid or SAA reduces the total error of the classification. The results presented in Table 4 and

What is claimed is:

1. An in vitro method for specific and sensitive diagnosis of rheumatoid arthritis in a patient, the method comprising measuring in a sample from the patient a concentration of anti-cyclic citrullinated peptide (anti-CCP) autoantibody and a concentration of interleukin 6, mathematically combining the concentrations into a single combined value, comparing the combined value to a multivariate cut-off level for a marker panel consisting of anti-CCP autoantibody and interleukin 6 determined in a reference population to be determinative of rheumatoid arthritis, and diagnosing rheumatoid arthritis where the combined value is greater than the multivariate cut-off level.

2. The method of claim 1 wherein the measuring step further includes measuring in the sample a concentration of serum amyloid A (SAA) and wherein the marker panel consists of anti-CCP antibody, interleukin 6, and SAA.

3. A kit for performing the method of claim 1 comprising reagents required to measure the concentrations of anti-CCP and interleukin 6 in said sample.

4. A kit for performing the method of claim 2 comprising reagents required to measure the concentrations of anti-CCP, interleukin 6, and SAA in said sample.

* * * * *